United States Patent [19]

Rózsa et al.

[11] Patent Number: 4,965,259

[45] Date of Patent: Oct. 23, 1990

[54] DIOXAZOCINE DERIVATIVES COMPOSITIONS AND METHODS CONTAINING THEM HAVING ANTIDEPRESSIVE, SPASMOLYTIC, ANTICONVULSIVE, AND ANTIARRHYTHMIC PROPERTIES

[75] Inventors: László Rózsa; Lujza Petöcz; Enikö Szirt née Kiszelly; Márton Fekete; Mária Szécsey née Hegedüs; Gábor Gigler; István Gacsályi, all of Budapest, Hungary

[73] Assignee: EGIS Gyógyszergyár, Budapest, Hungary

[21] Appl. No.: 292,450

[22] Filed: Dec. 30, 1988

[30] Foreign Application Priority Data

Dec. 31, 1987 [HU] Hungary .................. 6170/87

[51] Int. Cl.$^5$ .................. A61K 31/395; C07D 273/01
[52] U.S. Cl. .................. 514/183; 540/468
[58] Field of Search .................. 540/468; 514/183

[56] References Cited

U.S. PATENT DOCUMENTS

| | | | |
|---|---|---|---|
| 2,921,069 | 1/1960 | Ullyot | 540/597 X |
| 3,258,459 | 6/1966 | Yale et al. | 540/468 X |
| 3,803,143 | 4/1974 | Tanaka et al. | 540/468 |
| 3,989,717 | 11/1976 | Heath-Brown | 540/481 |
| 4,208,410 | 6/1980 | Rozsa et al. | 540/468 X |
| 4,229,350 | 10/1980 | Rozsa | 540/468 |
| 4,906,622 | 3/1990 | Rozsa et al. | 514/183 |

FOREIGN PATENT DOCUMENTS 2001980 2/1979 United Kingdom ............. 540/468

OTHER PUBLICATIONS

Flynn et al., J. Am. Chem. Soc., vol. 77, pp. 3104–3106 (06/05/55).

Primary Examiner—Diana G. Rivers
Attorney, Agent, or Firm—Keil and Weinkauf

[57] ABSTRACT

Dioxazocine derivatives, their preparation and composition containing them, said derivatives being represented by the formula I

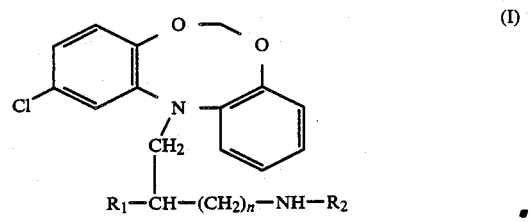

wherein
$R_1$ represents hydrogen or alkyl having from 1 to 4 carbon atoms,
$R_2$ represents alkyl having from 1 to 4 carbon atoms, and
n is equal to 0 or 1,
and pharmaceutically acceptable acid addition salts thereof formed with an inorganic or organic acid.

Two different reactions are described for making these compounds. They can be formulated into pharmaceutical compositions in the usual manner and exhibit central nervous system affecting activities.

13 Claims, No Drawings

DIOXAZOCINE DERIVATIVES COMPOSITIONS AND METHODS CONTAINING THEM HAVING ANTIDEPRESSIVE, SPASMOLYTIC, ANTICONVULSIVE, AND ANTIARRHYTHMIC PROPERTIES

This invention relates to dioxazocine derivatives, their preparation and compositions containing them. The new dibenzo[d,g][1,3,6]dioxazocine derivatives are encompassed by the formula I and pharmaceutically acceptable acid addition salts thereof formed with an inorganic or organic acid:

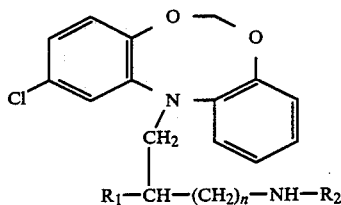

(I)

wherein
$R_1$ represents hydrogen or alkyl having from 1 to 4 carbon atoms,
$R_2$ represents alkyl having from 1 to 4 carbon atoms, and
n is equal to 0 or 1.

If $R_1$ is hydrogen, the compounds may exist in the form of optical isomers.

The compounds of the formula I possess valuable central nervous system effecting activities.

GB-P No. 2,001,980 describes analogous 12-(dialkylaminoalkyl)-dioxazocine derivatives of the formula VI:

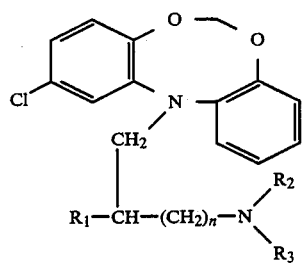

(VI)

wherein neither $R_2$ nor $R_3$ may represent hydrogen. These compounds are effective local anaesthetics and can be used for treating Parkinson syndrome.

In the specification and the claims the term "alkyl having from 1 to 4 carbon atoms" encompasses straight or branched chained alkyl groups, e.g. methyl, ethyl, n-propyl, isopropyl, n-butyl, sec.-butyl, tert.-butyl or isobutyl.

The compounds of the formula I and their pharmaceutically acceptable acid addition salts can be prepared by
(a) reacting a compound of the formula IV

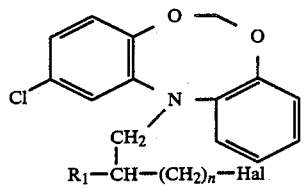

(IV)

wherein
$R_1$ and n are as defined above, and
Hal represents halo, with an alkylamine of the formula V $$H_2N-R_2$$

wherein
$R_2$ is as defined above, or
(b) reacting a compound of the formula VI

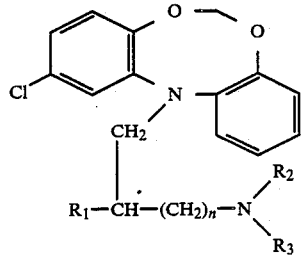

(VI)

wherein
$R_1$, $R_2$ and n are as defined above, and
$R_3$ represents alkyl having from 1 to 4 carbon atoms, with a chloroformate of the formula VII $$Cl-COOA \qquad (VII)$$

wherein A represents alkyl having from 1 to 4 carbon atoms or aralkyl containing 1 to 4 carbon atoms in the alkyl moiety, and then hydrolizing a thus-obtained urethane of the formula VII

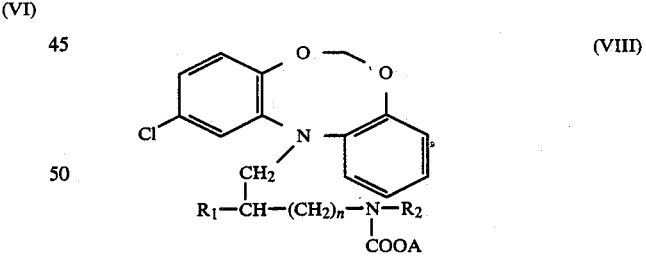

(VIII)

wherein $R_1$, $R_2$, n and A are as defined above.

In each case one may convert a compound of the formula I obtained into an organic or inorganic pharmaceutically acceptable acid addition salt, or convert such an acid addition salt into the free base of formula I.

In the process variant (a) 12-(omega-haloalkyl)-dioxazocines having the formula IV are reacted with amines of the formula V generally in the presence of an excess of the latter. It is suitable to carry out this reaction in the presence of an alkaline metal halide as catalyst. As alkaline metal halide e.g. sodium chloride, sodium bromide, sodium iodide or potassium iodide can be used. The reaction is carried out in the presence of a polar, apolar or dipolar organic solvent or in a mixture thereof. As polar organic solvent e.g. acetone, methyl ethyl ketone or alcohols, as apolar organic solvent e.g. benzene or toluene and as dipolar organic solvent e.g. N,N-dimethyl formamide can be used. The reaction is carried out generally at a temperature between 20° and 110° C., preferably between 80° and 90° C.

The starting materials of the formula IV can be prepared by reacting the dioxazocine of the formula II

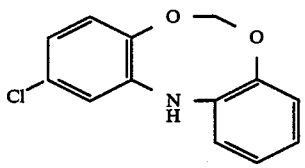

(II)

with an alpha,omega-dihaloalkane of the formula III

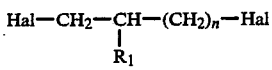

(III)

substantially in accordance with a method disclosed in the Hungarian patent specification No. 174,126. The intermediates of the formula III are suitably used in an excess, and a basic condensation agent, e.g. sodium hydroxide, sodium carbonate, potassium hydroxide, potassium carbonate or butyl lithium, is employed. As a solvent any of the solvents enumerated at process variant (a) above can be used. The reaction is carried out generally at a temperature between 20° and 150° C., preferably between 70° and 100° C.

The dioxazocine of the formula II can be prepared according to a method set forth in the Hungarian patent specification No. 174,126.

Process variant (a) of the present invention can be also carried out in such a manner that the starting material of the formula IV is reacted without separation, in the reaction mixture of its formation, with an amine of the formula V.

In process variant (b) compounds having the formula VI are reacted with chloroformates of the formula VII in the presence of an apolar organic solvent, e.g. benzene or toluene, generally at a temperature between 70° and 140° C., preferably between 70° and 90° C. A thus-formed urethane of the formula VIII is subjected to hydrolysis in the mixture of water and generally an alkanol, e.g. methanol, ethanol, n-propanol or isopropanol, in the presence of an alkaline metal hydroxide, e.g. sodium hydroxide, suitably at a temperature between 60° and 100° C., preferably between 75° and 85° C. The starting materials of the formula VI can be prepared according to a method disclosed in the Hungarian patent specification No. 174,126.

The compounds of the general formula I can be converted into acid addition salts by using anorganic or organic acids like sulphuric acid, hydrochloric acid, phosphoric acid, acetic acid, maleic acid, fumaric acid, lactic acid, propionic acid, etc. A free base of the formula I can be deliberated from such an acid addition salt by using an appropriate alkali.

The compounds of the formula I have valuable pharmacological activities, particularly sedative-tranquillant, antiepileptic, antidepressive, antiparkinsonic, anticonvulsive, antiarrhythmic and narcosis potentiating activities, as indicated by the following screening tests.

ACUTE TOXICITY ON WHITE MICE

Acute toxicity of the compounds was tested on white mice of both sexes from the strain CFLP in groups consisting of 10 animals weighing 18 to 22 g. The compounds to be tested were administered perorally in a volume of 20 ml/kg. After the administration, the mice were observed for 7 days while keeping them in plastic mouse boxes over a litter made of scrapings at room temperature. The animals could consume tap water and standard mouse feed ad libitum. The $LD_{50}$-values were determined according to Litchfield and Wilcoxon [J. Pharmacol. Exp. Ther., 96, 99 (1949)]. The results obtained are shown in Table I.

TABLE I

| Compound (Example No.) | $LD_{50}$ p.o. in mg/kg |
|---|---|
| 2 | 700 |
| 3 | 500 |
| 4 | 720 |

NARCOSIS POTENTIATING ACTIVITY (SLEEP INDUCED WITH HEXOBARBITAL ON MICE)

Groups consisting of 6 mice each were treated with the compound to be examined, perorally. After one hour, hexobarbital [5-(1-cyclohexenyl)-1,5-dimethyl-barbituric acid] was injected, intravenously, at a dosage of 40 mg/kg. The control group was treated only with hexobarbital to provoke sleep. The duration of sleep was recorded. If the duration of sleep of an animal exceeded that of the mean value of the control group by a factor of 2,5, it was considered as a positive reaction. From the data referring to the animals indicating a positive reaction, the $ED_{50}$-value was calculated. From the values of $LD_{50}$ and $ED_{50}$, the therapeutical index was determined for each compound tested. In the test, meprobamate [2-methyl-2-propylpropandiol-1,3-dicarbamate], chlordiazepoxide [7-chloro-2-methylamino-5-phenyl-3H-1,4-benzodiazepine-4-oxide] and traboxopin [2-chloro-12-(3-dimethylamino-2-methylpropyl)-12H-dibenzo[d,g][1,3,6]dioxazocine] were used for comparison. The results obtained are summarized in Table II.

TABLE II

| Compound (Example No.) | $ED_{50}$ in mg/kg | Therapeutical index $LD_{50}/ED_{50}$ |
|---|---|---|
| 3 | 2.4 | 208 |
| meprobamate ($LD_{50} = 1100$ mg/kg) | 260.0 | 4.2 |
| chlordiazepoxide ($LD_{50} = 620$ mg/kg) | 10.0 | 62.0 |
| traboxopin ($LD_{50} = 270$ mg/kg) | 25.0 | 10.8 |

From the data given in Table II it can be seen that the therapeutical index of the compound prepared in Example 3 is several times higher than that of the known reference compounds.

MOTILITY INHIBITING ACTIVITY

The tests were performed according to the method of Borsy et al. [Arch. Int. Pharmacolyn., 124, 1-2 (1960)]. Groups consisting of 3 mice each were treated, perorally, with different doses of the compounds to be tested. Then the test animals were placed in a Dews equipment. In this equipment the number of interruptions of infrared beam within 30 minutes was counted. The percentual deviation from the number of interruptions in the case of the control group was determined in each group, then the $ED_{50}$-values and therapeutical indexes were calculated. The results obtained are shown in Table III.

TABLE III

| Compound (Example No.) | $ED_{50}$ in mg/kg | Therapeutical index $LD_{50}/ED_{50}$ |
| --- | --- | --- |
| 3 | 27 | 18.50 |
| meprobamate | 270 | 4.1 |
| chlordiazepoxide | 60 | 10.3 |
| traboxopin | 25 | 10.8 |

ANTAGONISM OF TETRABENAZINE PTOSIS ON MICE

The tests were performed according to the method of Hoffmeister et al. which was adapted to mice [Arzneim.-Forschung, 19, 846–858 (1969)]. Groups consisting of 10 mice each were treated, perorally, with different doses of the compounds to be tested. The control group was treated only with the corresponding carrier. After 30 minutes, tetrabenazine [3-isobutyl-9,10-dimethoxy-1,2,3,4,6,7-hexahydrobenzo[a]quinolizine-2-one] was administered intraperitoneally at a dosage of 50 mg/kg. The number of animals having closed palpebral fissure was determined in each group after 30, 60, 90 and 120 minutes. Then, the mean value of ptosis was calculated in each group, and the deviation from that of the control group (i.e. the inhibition) was expressed in percentage. From the data obtained, the $ED_{50}$-value and the therapeutical index were determined for each novel compound tested as well as for amitryptiline [5-(3-dimethylaminopropylidine)-10,11-dihydro-5H-dibenzo[a,d]cycloheptene hydrochloride] and traboxopin [2-chloro-12(3-dimethylamino-2-methylpropyl)-12H-dibenzo[d,g][1,3,6]dioxazocine] employed for comparison. The results obtained are shown in Table IV.

TABLE IV

| Compound (Example No.) | $ED_{50}$ in mg/kg | Therapeutical index $LD_{50}/ED_{50}$ |
| --- | --- | --- |
| 4 | 7.3 | 98.6 |
| amitryptiline | 12.0 | 18.7 |
| traboxopin | it cannot be determined, toxic interactions with tetrabenazine | |

The therapeutical index of the compound of the invention is more than five times higher than that of the amitryptiline widely used in the clinical praxis with good results.

INHIBITION OF TREMOR INDUCED BY TREMORINE ON MICE

The tests were carried out according to Everett [Science, 124, 79 (1956)]. Tremor was induced by tremorine [1,1'-(2-butynylene)-dipyrrolidine] administered intraperitoneally at a dosage of 20 mg/kg. The compounds to be examined were given perorally to the animals one hour prior to the administration of tremorine, and the tremor developed was evaluated 45 minutes after the administration of tremorine. The results are set forth in Table V.

TABLE V

| Compound (Example No.) | $ED_{50}$ in mg/kg | Therapeutical index $LD_{50}/ED_{50}$ |
| --- | --- | --- |
| 2 | 5.2 | 134.6 |
| 3 | 6.4 | 78.1 |
| trihexyphenidyl | 15.0 | 24.3 |
| traboxopin | 25.0 | 10.8 |

From Table V it can be concluded that the therapeutic index of the compounds of the invention strongly surpasses that of the known compounds used for comparison.

SPASMOLYTIC ACTION ON MICE

The tests were carried out according to the method of Banzinger and Hane which was adapted to white mice [Arch. Int. Pharmacolyn., 167, 245–249 (1959)]. The test animals were treated perorally with the compounds to be tested. One hour after the administration pentetrazole (6,7,8,9,-tetrahydro-5H-tetrazolozepine) was given intraperitoneally in a dosis of 125 mg/kg. The tonic-extensoric spasms on the hind limbs were registered. As reference compound 5-ethyl-5-phenylbarbituric acid (phenobarbital), 3,5,5-trimethyl-oxazolidine-2,4-dione (trimetadione) and traboxopin were used. The results are set forth in Table VI.

TABLE VI

| Compound (Example No.) | $ED_{50}$ in mg/kg | Therapeutical index $LD_{50}/ED_{50}$ |
| --- | --- | --- |
| | 19 | 26.3 |
| 4 | 25 | 28.8 |
| phenobarbital | 19 | 8.8 |
| trimetadione | 400 | 5.5 |
| traboxopin | 32 | 8.4 |

From Table VI it can be concluded that the therapeutic index of the compounds of the invention strongly surpasses that of the known compounds used for comparison.

ANTICONVULSIVE ACTIVITY ON MICE

The tests were carried out according to the method of Swinyard et al. [I. Pharmacol. Exp. Ther., 106, 319–330 (1952)] which method is based on the inhibition of electroshock provoked by electric current on mice. The compounds to be tested were administered perorally. One hour later electroshocks were given by using corneal electrodes. The frequency of the electroshocks was 50 Hz, the current intensity 45 mA and the duration 0.4 sec. The full inhibition of the tonic-extensoric spasm on the hind limbs was considered as the criterium of the anticonvulsive activity. As reference compound phenobarbital, trimetadone and traboxopin were used. The results are set forth in Table VII.

TABLE VII

| Compound (Example No.) | $ED_{50}$ in mg/kg | Therapeutical index $LD_{50}/ED_{50}$ |
| --- | --- | --- |
| 4 | 40 | 19 |
| phenobarbital | 24.5 | 6.8 |
| trimetadione | 490 | 4.3 |
| traboxopin | 54 | 5.0 |

From Table VII it can be concluded that the therapeutic index of the compound of Example 4 is about 3–5-fold higher than that of the reference compounds.

ANTIARRHYTHMIC ACTIVITY ON RATS

The antiarrhythmic activity of the novel compounds was examined by influencing the arrhythmia provoked by aconitine on rats weighing 160 to 200 g according to a modified method of Marmo et al. [Arzneim.-Forsch., 20, 12 (1970)]. The animals were anaesthetized by the administration of 1.2 g/kg of ethyl urethane, intraperitoneally. Aconitine was given at a dosage of 75 μg/kg, intravenously. The compounds to be tested were administered perorally 30 minutes prior to the treatment with aconitine. The inhibition observed is shown in Table VIII in percentage. In the test, lidocaine and quinidine was employed for comparison.

TABLE VIII

| Compound (Example No.) | Dose in mg/kg | Inhibition in percentage |
| --- | --- | --- |
| 4 | 4 | 90.9 |
| lidocaine | 4 | 23.4 |
| quinidine | 4 | 27.3 |

From Table VIII it appears that the compound of Example 4 has an inbiting action of 90% in a dosis of 4 mg/kg (its $ED_{50}$-value is equal to 3.44), while the reference compounds possess an inbiting action lower than 30%.

From the above pharmacological test results it can be concluded that the novel compounds of the formula (I) or the pharmaceutically acceptable acid addition salts thereof can be used primarily for affecting the central nervous system and as antiarrhytmic agents.

The compounds of the formula I and pharmaceutically acceptable acid addition salts thereof can be converted into pharmaceutical compositions, in a manner known per se, by using conventional carriers and optionally other known additives. Generally compositions suitable for oral, parenteral or topical application are prepared.

The solid pharmaceutical compositions suitable for oral administration, e.g. tablets, capsules, dragées, etc. may contain binding agents like gelatine, sorbite, polyvinyl pyrrolidone, etc.; fillers like lactose, saccharose, starch, calcium phosphate, etc.; tabletting agents like magnesium stearate, talc, polyethylen glycol, silicon dioxide, etc.; wetting agents like sodium lauryl sulphate, etc. The liquid pharmaceutical compositions suitable for oral administration, e.g. solutions or suspensions may contain suspending agents like sorbite, saccharose solution, gelatine, carboxymethyl cellulose, etc.; emulgeating agents like sorbitan monooleate; solvents like oils, oily esters, glycerine, propylene glycol, ethanol, etc.; conserving agents like methyl parabene.

The pharmaceutical compositions suitable for parenteral administration are generally sterile solutions.

If desired, the above-mentioned pharmaceutical compositions may contain known flavouring and colouring agents.

Further details of the invention are illustrated by the following non-limiting Examples.

EXAMPLE 1

2-Chloro-12-(3-chloropropyl)-12H-dibenzo[d,g][1,3,6-]dioxazocine

A mixture of 14.9 g. (0.06 moles) of 2-chloro-12H-dibenzo[d,g][1,3,6]dioxazocine, 37.8 g. (0.24 moles) of 1-bromo-3-chloropropane, 19.6 g. (0.48 moles) of sodium hydroxide and 180 ml. of methyl ethyl ketone is stirred under reflux for 10 hours. Thereafter further 19.6 g. (0.48 moles) of sodium hydroxide are added and the stirring under reflux continued for 10 hours. The reaction mixture is cooled to 20° C. and poured to 300 g. of broken ice under stirring. 100 ml. of benzene are added, the organic phase is separated and the solvent is removed in vacuo. The residue is subjected to vacuum destillation. There are obtained 14.3 g. of a yellow viscous liquid, b.p./0.3 mmHg: 165° to 171° C. This liquid solidifies upon trituration with petrol ether. Recrystallization from isopropanol affords 12.5 g. (64.0%) of a white product, melting at 105° to 108° C.

Analysis for $C_{16}H_{15}Cl_2NO_2$ (molecular weight: 324.209): Calculated: C 59.28%, H 4.66%, Cl 21.87%, N 4.32%; Found: C 59.08%, H 4.93%, Cl 21.78%, N 4.30%.

EXAMPLE 2

2-Chloro-12-(3-isopropylaminopropyl)-12H-dibenzo[d,g][1,3,6]dioxazocine maleate

A mixture of 32.4 g. (0.10 moles) of 2-chloro-12-(3-chloropropyl)-12H-dibenzo[d,g][1,3,6]dioxazocine prepared by the method of Example 1, 11.8 g. (0.20 moles) of isopropyl amine, 7.5 g. of sodium iodide and 200 ml. of methyl ethyl ketone is stirred under reflux for 20 hours. Thereafter the solvent is removed in vacuo, 100 ml. of benzene are added to the residue and the mixture obtained is washed with water. Thereafter 37.5 g. (0.25 moles) of tartaric acid and 150 ml. of water are added to the organic phase and the reaction mixture is stirred for 30 minutes. The aqueous phase is separated, 150 ml. of methylene chloride are added thereto and the pH is adjusted to 10 by using aqueous ammonia. The organic phase is separated and the solvent is removed. The residue is dissolved in 100 ml. of isopropanol and a solution of 9.5 g (0.82 moles) of maleic acid is added thereto. The precipitated white product is filtered off, dried and recrystallized from isopropanol. There are obtained 32.4 g. (70.0%) of the title product, melting at 126° to 129° C.

Analysis for $C_{23}H_{27}ClN_2O_6$ (molecular weight: 462.899): Calculated: C 59.68%, H 5.88%, Cl 7.66%, N 6.05%; Found: C 59.86%, H 6.21%, Cl 7.59%, N 5.89%.

EXAMPLE 3

2-Chloro-12-(3-methylamino-2-methylpropyl)-12H-dibenzo[d,g][1,3,6]dioxazocine hydrochloride (A) A solution of 96.3 g. (0.277 moles) of 2-chloro-12-(3-dimethylamino-2-methylpropyl)-12H-dibenzo[d,g][1,3,6]dioxazocine in 100 ml. of dry benzene is heated up to boiling and a solution of 90.3 g. (0.832 moles) of ethyl chloroformate in 90 ml. of benzene are added thereto during 20 minutes. The reaction mixture is refluxed for 4 hours, cooled to 20° C. and washed with 120 ml. of water. The organic phase is separated and washed twice with 120 ml. of a 5% aqueous solution of tartaric acid each. The benzene solution is dried over dry magnesium sulphate, the solvent is removed in vacuo and the residue is crystallized from ethanol. Recrystallization from isopropanol affords 99.8 g. (89%) of 2-chloro-12-[N-(ethoxycarbonyl)-N-methylamino-2-methylpropyl]-12H-dibenzo[d,g][1,3,6]dioxazocine, melting at 94° to 96° C.

Analysis for $C_{21}H_{25}ClN_2O_4$ (molecular weight: 404.895): Calculated: C 62.30%, H 6.22%, Cl 8.76%, N 6.92%; Found: C 62.10%, H 6.72%, Cl 8.86%, N 7.00%.

(B) A mixture of 60.0 g. (0.148 moles) of the compound prepared in accordance with the method of part (A) of the present Example, 49.7 g. (0.88 moles) of potassium hydroxide and 140 ml of ethanol of 96% strength is boiled in a flask equipped with a mixer and reflux condenser for 20 hours. The solvent is removed in vacuo and the residue is stirred in a mixture of 150 ml. of benzene and 300 ml. of water. The aqueous phase is separated, 150 ml. of benzene are added thereto and the pH is adjusted to 10 by using aqueous ammonia. The organic phase is separated and the solvent is removed. The residue is dissolved in 180 ml. of isopropanol and the pH of the solution is adjusted to 2 by using a solution of dry hydrogen chloride gas in isopropanol. The precipitated product is filtered off and dried. Recrystallization from isopropanol affords 46.0 g. (86%) of the title product, melting at 147° to 149° C.

Analysis for $C_{18}H_{22}Cl_2H_2O_2$ (molecular weight: 369.292): Calculated: C 58.54%, H 6.01%, Cl 19.20%, N 7.59%; Found: C 58.81%, H 6.18%, Cl 19.25%, N 7.52%.

EXAMPLE 4

2-Chloro-12-(3-methylaminopropyl)-12H-dibenzo[d,g][1,3,6]dioxazocine maleate

One proceeds substantially in the same manner as in part (A) of Example 3 except that 60.0 g (0.18 moles) of 2-chloro-12-(3-dimethylaminopropyl)-12H-dibenzo[d,g][1,3,6]dioxazocine are used as starting material. The thus-obtained N-(ethoxycarbonyl)-derivative is subjected without separation to the hydrolysis step described in part (B) of Example 3. The obtained free base corresponding to the title compound is converted into a salt with maleic acid in isopropanol. Recrystallization from isopropanol affords 43.8 g. (76.4%) of the title product, melting at 157° to 160° C.

Analysis for $C_{21}H_{23}ClN_2O_6$ (molecular weight: 434.845): Calculated: C 58.00%, H 5.33%, Cl 8.15%, N 6.44%; Found: C 57.89%, H 5.62%, Cl 8.18%, N 6.35%.

We claim:

1. A compound of the formula I

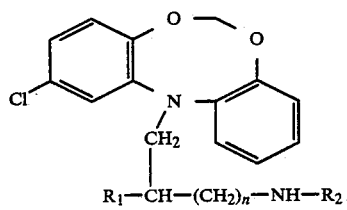

(I)

wherein $R_1$ represents hydrogen or methyl, $R_2$ represents an alkyl having from 1 to 3 carbon atoms, and n is equal to 1, and pharmaceutically acceptable acid addition salts thereof formed with an inorganic or organic acid.

2. A compound as defined in claim 1, wherein $R_2$ is isopropyl or methyl.

3. 2-Chloro-12-(3-isopropylaminopropyl)-12H-dibenzo[d,g][1,3,6]dioxazocine and pharmaceutically acceptable acid addition salts thereof.

4. 2-Chloro-12-(3-methylamino-2methylpropyl)-12H-dibenzo[d,g][1,3,6]dioxazocine and pharmaceutically acceptable acid addition salts thereof.

5. 2-Chloro-12-(3-methylaminopropyl)-12H-dibenzo[d,g][1,3,6]dioxazocine and pharmaceutically acceptable acid addition salts thereof.

6. A pharmaceutical composition having antidepressive, spasmolytic, anticonvulsive and antiarrhythmic properties comprising an effective amount of a compound or salt as defined in claim 1 and a pharmaceutical carrier or excipient.

7. A pharmaceutical composition having antidepressive, spasmolytic, anticonvulsive and antiarrhythmic properties which comprises an effective amount of the compound or salt as defined in claim 3 and a pharmaceutically acceptable carrier or excipient.

8. A pharmaceutical composition having antidepressive, spasmolytic, anticonvulsive and antiarrhythmic properties which comprises an effective amount of the compound or salt as defined in claim 4 and a pharmaceutically acceptable carrier or excipient.

9. A pharmaceutical composition having antidepressive, spasmolytic, anticonvulsive and antiarrhythmic properties which comprises an effective amount of the compound or salt as defined in claim 5 and a pharmaceutically acceptable carrier or excipient.

10. A method of treating a patient for depression which comprises: administering to said patient an effective amount of a pharmaceutical composition as defined in claim 6.

11. A method of treating a patient for arrhythmia which comprises: administering to said patient an effective amount of a pharmaceutical composition as defined in claim 6.

12. A method of treating a patient for epileptic spasms which comprises: administering to said patient an effective amount of a pharmaceutical composition as defined in claim 6.

13. A method of treating a patient for convulsions which comprises: administering to said patient an effective amount of a pharmaceutical composition as defined in claim 6.

* * * * *